(12) United States Patent
Kisaka et al.

(10) Patent No.: US 6,727,411 B2
(45) Date of Patent: Apr. 27, 2004

(54) METHOD OF PRODUCING TRANSGENIC PLANTS HAVING IMPROVED AMINO ACID COMPOSITION

(75) Inventors: Hiroaki Kisaka, Kawasaki (JP); Takao Kida, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 428 days.

(21) Appl. No.: 09/727,758

(22) Filed: Dec. 4, 2000

(65) Prior Publication Data

US 2003/0101487 A1 May 29, 2003

(30) Foreign Application Priority Data

Dec. 13, 1999 (JP) .............................. 11-352552

(51) Int. Cl.⁷ ...................... C12N 15/29; C12N 15/82; A01H 1/00; A01H 5/00; A01H 5/10
(52) U.S. Cl. .................... 800/317.4; 800/278; 800/286; 800/298; 800/294; 800/300; 536/23.1; 536/23.2; 536/23.6; 536/24.5
(58) Field of Search ................ 800/278, 286, 800/298, 317.4, 294, 300; 536/23.1, 23.6, 24.5, 23.2

(56) References Cited

U.S. PATENT DOCUMENTS 5,876,983 A 3/1999 Sugimoto et al.
5,919,694 A 7/1999 Sugimoto et al.

OTHER PUBLICATIONS

Fourgoux–Nicol et al 1999, Plant Molecular Biology 40 : 857–872.*
Elomaa P. et al., Molecular Breeding 1996, 2: 41–50.*
Mate C. et al., 1996 Planta 198: pp. 604–613.*
Gaffe J. et al. Plant Physiology, 1994; vol. 105; pp. 199–203.*
Smith C. et al.; Nature 1988, 334: 724–726.*
V. Satya Narayan, et al., Phytochemistry, vol. 29, No. 2, pp. 367–375, "Metabolism, Enzymology and Possible Roles of 4–Aminobutyrate in Higher Plants", 1990.
Pedro P. Gallego, et al., Plant Molecular Biology, No. 27, pp. 1143–1151, "A Role for Glutamate Decarboxylase During Tomato Ripening: The Characterisation of a cDNA Encoding a Putative Glutamate Decarboxylase with a Calmodulin–Binding Site", 1995.
Gideon Baum, et al., The EMBO Journal, vol. 15, No. 12, pp. 2988–2996, "Calmodulin Binding to Glutamate Decarboxylase is Required for Regulation of Glutamate and GABA Metabolism and Normal Development in Plants", 1996.
Miroyah Zik, et al., Plant Molecular Biology, No. 37, pp. 967–975, "Two Isoforms of Glutamate Decarboxylase in Arabidopsis are Regulated by Calcium/Calmodulin and Differ in Organ Distribution", 1998.

* cited by examiner

*Primary Examiner*—David T. Fox
*Assistant Examiner*—Russell Kallis
(74) *Attorney, Agent, or Firm*—Oblon, Spivak, McClelland, Maier & Neustadt, P.C.

(57) ABSTRACT

Transgenic plants containing free amino acids, particularly at least one amino acid selected from among glutamic acid, asparagine, aspartic acid, serine, threonine, alanine and histidine accumulated in a large amount, in edible parts thereof, and a method of producing them are provided.

In this method, glutamate decarboxylase(GAD) gene is introduced into a plant in anti-sense direction together with an appropriate regulatory sequence, and the expression of GAD gene is supressed.

14 Claims, 5 Drawing Sheets

1. λ-HindIII marker
2. Non-transgenic-tomato-1
3. Non-transgenic-tomato -2
4. pMAT037-1
5. pMAT037-2
6. pMAT037-3
7. GAD-No.1
8. GAD-No.2
9. GAD-No.6-2
10. GAD-No.11
11. 100bp marker

1. Non-transgenic tomato 1
2. Anti-T-gad-19 No. 1
3. Anti-T-gad-19 No. 2

FIG.5

METHOD OF PRODUCING TRANSGENIC PLANTS HAVING IMPROVED AMINO ACID COMPOSITION

BACKGROUND OF THE INVENTION

The present invention relates to a method of producing transgenic tomatoes having an increased free amino acid content, and transgenic tomatoes thus produced. In particular, the present invention relates to a method of producing transgenic tomatoes containing at least one of asparagine, aspartic acid, serine, threonine, alanine, histidine and glutamic acid accumulated in a large amount, and transgenic tomatoes produced by this method.

The technique of transforming a plant by introducing a particular gene thereinto was reported for the first time in the world in the study wherein it was achieved by introducing a gene into tobacco with *Agrobacterium tumefaciens*, a soil bacteria. Thereafter, many products having useful agricultural characteristics were produced, and it was also tried to produce useful components in plants. A plant breeding method by such a recombinant DNA technique is considered to be hopeful in place of the ordinary, traditional technique of developing varieties of plants. In this field, improvement in the characteristics of plants concerning nitrogen assimilation is also being studied. The study of amino acids is particularly prospering because they are important ingredients of particularly fruits, root crops and seeds and also they exert a great influence on the tastes of them.

Reports on the biosynthesis of amino acids include, for example, a report that free lysine content of tobacco was increased to 200 times as high content by introduction of DHDPS gene derived from *E. coli* into tobacco (U.S. Pat. No. 5,258,300, Molecular Genetics Res. & Development); a report that free lysine content was increased by introduction of AK gene (EP 485970, WO 9319190); a report that asparagine content was increased to 100 times as high content by introduction of AS gene into tobacco; and a report that tryptophan content was increased to 90 times as high content by introduction of an anthranilic acid-synthesizing enzyme into a rice plant (WO 9726366, DEKALB Genetic Corp). The plants into which a gene is to be introduced are not limited to model plants such as tobacco and *Arabidopsis thaliana* but plants which produce fruits such as tomato are also used. For example, as for tomatoes, a transformant thereof was obtained by Agrobacterium co-cultivation method in 1986 [S. McCormick, J. Niedermeyer, J. Fry, A. Barnason, R. Horsch and R. Freley, Plant Cell Reports, 5, 81–84 (1986); Y. S. Chyi, R. A. Jorgenson, D. Goldstern, S. D. Tarksley and F. Loaiza-Figueroe, Mol. Gen. Genet., 204, 64–69 (1986)]. Since then, investigations were made for the improvement of the recombinant DNA techniques. Various genes relating to the biosynthesis of amino acids and nitrogen assimilation other than those described above are also known. They include asparaginase and GOGAT, and the nucleotide sequences of them were also reported.

Glutamic acid which is one of α-amino acids is widely distributed in proteins. It is generally known that a tasty component of tomatoes used as a seasoning and also a tasty component of fermentation products of soybeans (such as soy sauce and fermented soy paste) are glutamic acid. It is also known that glutamic acid is synthesized in the first step of nitrogen metabolism in higher plants. It is also known that glutamine and asparagine formed from glutamic acid are distributed to tissues through phloem and used for the synthesis of other amino acids and proteins. It was reported that in plants, glutamic acid exists in a high concentration in phloem through which photosynthesis products such as sucrose and amino acids are transported [Mitsuo Chino et al., "Shokubutsu Eiyo/ Hiryogaku" p. 125 (1993)]. As for examples of glutamic acid contained in a high concentration in edible parts of plants, it is known that about 0.25 g/100 gf. w. of glutamic acid is contained in tomato fruits ["Tokimeki" No. 2, Nippon Shokuhin Kogyo Gakkaishi, Vol. 39, pp. 64–67 (1992)]. However, glutamic acid of a high concentration cannot be easily accumulated in plant bodies because it is a starting material for amino group-donors and also it is metabolized in various biosynthetic pathways as described above even though the biosynthesizing capacity of the source organs can be improved.

As far as the applicant knows, it was not yet succeeded to remarkably increase glutamic acid concentration in edible parts of plants by either cross breeding or gene manipulation. For example, although transgenic plants were produced by the introduction of GDH (glutamate dehydrogenase) gene, it was reported that when glutamate dehydrogenase GDH (NADP-GDH) gene derived from *Escherichia coli* was introduced into tobacco and corn for the purpose of imparting resistance to phosphinothricin used as a herbicide, glutamic acid content of the roots of them was only increased to 1.3 to 1.4 times as high [Lightfoot David et al. CA2180786 (1966)]. Namely, in this report, glutamic acid content of tobacco roots was merely increased from 14.7 mg/100 gf. w. to 20.6 mg/100 gf. w., and that of corn roots was increased from 16.2 mg/100 gf. w. to 19.1 mg/100 gf. w. Although there are other reports on the use of GDH gene, no example is given therein [WO 9509911, α,β-subunits derived from chlorella (WO 9712983)]. In addition, no analytical value of amino acids of glutamic acid group was given therein.

In the first step of the assimilation of inorganic nitrogen into an organic substance, ammonia is incorporated into glutamic acid for mainly forming glutamine. This process is catalyzed by glutamine synthetase enzyme (GS). Then glutamine is reacted with α-ketoglutaric acid in the presence of glutamate synthase (GOGAT) to form two molecules of glutamic acid. This GS/GOGA cycle is considered to be the main pathway of the nitrogen anabolism in plants [Miflin and Lea, Phytochemistry 15; 873–885 (1976)]. It is known that the ammonia anabolism proceeds also by a metabolic pathway other than the pathway wherein ammonia incorporation is catalyzed by GS [Knight and Langston-Unkefer, Science, 241: 951–954 (1988)]. Namely, in this metabolic pathway, ammonia is incorporated into α-ketoglutaric acid to form glutamic acid. This process is catalyzed by glutamate dehydrogenase (GDH). However, plant GDH has a high Km value for ammonia. The role of this pathway under normal growing conditions has not yet been elucidated enough because ammonia is toxic and the concentration of intracellular ammonia is usually low. A researcher reported that this pathway contributes to the nitrogen anabolism when intracellular ammonium concentration is increased over a normal level (Knight and Langston-Unkefer, supra).

Glutamic acid thus synthesized is further utilized for the synthesis of other amino acids such as asparagine, alanine, phenylalanine, leucine, isoleucine, glycine, valine, serine, tyrosine, proline and γ-aminobutyric acid (GABA). It is particularly known that GABA is accumulated in storage organs such as tomato fruits and sugar beat roots. From this fact, the consumption of glutamic acid is supposed. It is also known that the accumulation of GABA is induced by environmental stresses such as the acidity in the cell, low temperature and heat shock [Streeter and Thimpson, Plant Physiol., 49, 572–578 (1972): Raggiani et al., Plant Cell Physiol., 29; 981–987 (1988): Menengus et al., Plant Physiol., 90; 29–32 (1989): Roberts et al., Plant Physiol., 98; 480–487 (1992): Shelp et al., Plant Physiol., 94; 219–228 (1995): Aurisano et al., Plant Cell Physiol. 36; 1525–1529 (1995): Wallace et al., Plant Physiol., 75; 170–175 (1990): and Mayer et al., Plant Physiol., 94; 796–810]. GABA is synthesized from glutamic acid by the catalyzing function of glutamate decarboxylase (GAD). The activity of GAD is controlled by intracellular Ca(calcium) ion concentration and calmodulin [Ling et al., Plant Cell, 6; 1135–1143 (1994): Snedden et al., Plant Physiol., 108; 543–549 (1995): Arazi et al., Plant Physiol., 108; 551–561 (1995): and Snedden et al., J. Biol. Chem, 271; 4148–4153 (1996)]. It is considered that the change in the intracellular Ca ion concentration is induced by various stresses to rapidly increase GAD activity. As a result, the action of GABA as a signal-transducing substance in plant cells is expected, but the details thereof have not yet been elucidated.

A gene encoding GAD was isolated from a petunia for the first time [Baum et al., J. Biol. Chem., 268; 19610–19617 (1995)]. Then GAD gene was isolated from tomatoes [Gallego et al., Plant Mol. Biol., 27; 1143–1151 (1995)] and Arabidopsis [Zik et al., Plant. Mol. Biol., 37; 967–975 (1998)]. In all the cases, calmodulin-binding site comprising 30 to 32 amino acids is present at C-terminal in common. However, the organs where the gene expression was found vary depending on kinds of the plants. In petunias, the organs are flower petals and flowers and in tomatoes, the organs are fruits. It was also reported that GAD 1 genes were expressed in roots and GAD 2 genes were expressed in the whole plant body of Arabidopsis.

Gideons et al [EMBO, 15; 2988–2996 (1996)] introduced GAD genes isolated from petunia into tobacco to obtain a transformant for the purpose of investigating regulatory function of calmodulin on GAD expression. According to their report, they made two kinds of tests. In one of the tests, the whole GAD gene length was introduced in the sense direction and in another test, the introduction was conducted in the same manner but the calmodulin-binding site was removed. The transformants were examined to find that GABA was increased and glutamic acid was decreased in amount in each cases. The degree of the change in amount was higher in the case in which calmodulin-bonding site was removed. It was also reported that the height of the plants was shortened and morphologic difference was observed.

SUMMARY OF THE INVENTION

The object of the present invention is to provide a method of increasing free amino acid contents of storage organs of plants, in particular, a method of increasing at least one of free amino acids selected from the group consisting of glutamic acid, asparagine, aspartic acid, serine, threonine, alanine and histidine contained in edible parts such as roots and seeds of plants; and also to provide transgenic plants in which said free amino acids are accumulated in a large amount.

The object of the present invention is attained by providing a plant having a changed expression level of a major enzyme concerning the assimilation and utilization of nitrogen and/or a plant having an organ-specific expression, and a method of producing such a plant. The plant can be produced by introducing at least one gene encoding an enzyme which assimilates or utilizes nitrogen together with a suitable regulatory sequence and excessively expressing the same or controlling the expression thereof.

In particular, by introducing a glutamate decarboxylase (GAD) gene in antisense direction into the plant, free amino acids, particularly at least one of glutamic acid, asparagine, aspartic acid, serine, threonine, alanine and histidine are accumulated in a large amount in the plant.

Therefore, in a preferred embodiment, the method of the present invention comprises the step of
a) trasnforming a plant with a genetic construct containing an antisense sequence of a gene sequence encoding glutamate decarboxylase (GAD), a regulatory sequence capable of expressing the antisense sequence and a marker gene,
b) selecting or identifying the transgenic plant base on a character imparted by the marker gene in the genetic construct;
c) screening the transgenic plant in which one or more free amino acids are accumulated in a larger amount; and
d) selecting the transgenic plant in which one or more free amino acids are accumulated in a larger amount.

The present invention relates to the manipulation of a gene concerning nitrogen metabolism in plants. In particular, the present invention relates to a method of changing the expression level of an enzyme responsible for the assimilation and utilization of nitrogen for the purpose of accumulating a free amino acid, particularly glutamic acid which improves taste, in a large amount in edible parts such as fruits, roots (of root crops) and seeds of useful plants. By increasing, modifying or controlling the expression level of such an enzyme, plants having desired properties can be obtained.

DESCRIPTION OF THE PREFERRED EMBODIMENTS

One group of target genes used in the present invention consists of genes encoding enzymes concerning the metabolism from glutamic acid to GABA. An example of the target genes is glutamate decarboxylase (GAD). As for the manipulation, a plant is transformed with a nucleic acid assembly described herein. The transgenic plants or their progeny can express desired, modified enzyme activities and they are screened for changes in expression of corresponding mRNA, changes in the anabolism or utilization of nitrogen and/or an increase in free amino acid content of plants.

In short, the method of the present invention comprises the following steps, and the transgenic plants of the present invention are those produced by this method:
a) the step of cloning an intended gene;
b) the step of, if necessary, recloning the gene by inserting the obtained gene into a suitable vector in a suitable direction;
c) the step of introducing the vector into plant cells to obtain a transformant; and
d) the step of regenerating plants from the obtained transformant and culturing them.

In one of the embodiments of the present invention, one or several nucleotide sequences encoding an enzyme for assimilating or utilizing nitrogen or their antisense sequences are under the control of a strong constitutive promoter, and can be over-expressed in the plants.

In another embodiment of the present invention, the expression pattern of the enzyme for assimilating or utilizing nitrogen is modified. The expression pattern can be modified by the genetic manipulation of the plants by utilizing at least one of the followings:
a) a transgene in which a gene sequence encoding an enzyme or antisense sequence thereof is connected to a promoter having a desired expression pattern (such as a promoter having an organ-specific or developmental stage-specific expression pattern) in a functional state,
b) a modulating control gene which activates the expression in a preferred pattern of a gene encoding the enzyme or its antisense mRNA, and
c) an antisense sequence of one copy natural gene which has a regulatory site modified so as to be expressed in a preferred pattern.

In a still preferred embodiment of the present invention, a modified enzyme and/or enzyme of a different type are expressed in a pathway of nitrogen assimilation or nitrogen utilization. This embodiment involves the production of a genetic construction which can be expressed in plant cells and which encodes a corresponding enzyme having a catalytic action different from the catalytic action of the enzyme which assimilates or utilizes nitrogen in a host plant and also the gene manipulation with the gene constructs.

By this technique, plants containing free amino acids in an increased amount can be obtained.

For growing such plants, a conventional method of growing new varieties of plants is unsuitable because it necessitates screening of large isolated groups and a long time. However, according to the present invention, such a labor becomes unnecessary and the time can be saved.

The terms and abbreviations used herein are defined as follows:
35S: cauliflower mosaic virus promoter
GAD: glutamate decarboxylase
GDH: glutamate dehydrogenase
Fused gene construct: a genetic construct comprising a promoter in which heterologous genes are connected together (the promoter controls the transcription of heterologous genes)
Heterologous gene: In a gene construct, a heterologous gene means a gene which is connected to a promoter which is not naturally linked to the gene. The heterologous gene may be or may not be derived from the same organism which provides the promoter.
PCR: polymerase chain reaction.

Various genes such as described above are included in the genes for assimilating or utilizing nitrogen usable in the present invention. Glutamate decarboxylase (GAD) gene is one of examples of preferred enzymes usable for accumulating glutamic acid. When GAD gene is used, the gene is expressed in the antisense direction.

In a preferred embodiment of the present invention, a tomato plant is manipulated by a genetic engineering technique with a recombinant construct encoding tomato GAD gene connected in the antisense direction to cauliflower mosaic virus (CaMV) 35S promoter which is a powerful constitutive plant promoter. In the lines wherein GAD expression was suppressed, free amino acid content was increased as compared with that of the parent plant used as the control. In particular, glutamic acid content was increased to twice as much amount.

The nucleic acid construct usable in the present invention can be prepared by methods well known by those skilled in the art.

The details of a method wherein the constructs are isolated and the properties of them are determined and also a recombinant DNA techniques which can be employed for the manipulation and the preparation of the constructs are described in, for example, Sambrook et al., Molecular cloning-Laboratory manual, the second edition (Cold Spring Harbor Laboratory Press). When a nucleotide sequence of a desired component is known, it may be more advantageous not to isolate it from a biological source but to synthesize it in some cases. When the whole nucleotide sequence or a part thereof is known, a desired nucleic acid segment can be amplified. In such a case, those skilled in the art can refer to literatures such as Caruthers et al., Nuc. Acids. Res. Symp. Ser. 7: 215–233 (1980) and Kempe, Nuc. Acids. Res. 9: 2807–2817 (1981). In other cases, the intended component can be advantageously produced by polymerase chain reaction (PCR) amplification. As for PCR method, those skilled in the art can refer to Gelfand, "PCR Technique (The Theory and Application of DNA Amplification)" edited by H. A. Erlich and published by Stockton Press, N.Y. in 1989 and "Present Protocol in Molecular Biology" Vol. 2, Chapter 15 edited by Ausubel et al., and published by John Wiley & Sons in 1988.

The genetic construct used in the present invention may generally contain a suitable promoter which functions in plant cells, a suitable terminator such as nopaline synthetic enzyme gene terminator, other elements useful for controlling the expression and marker genes suitable for selecting the transgenic product such as drug-resistant genes, e. g. genes for resistance to kanamycin, G 418 or hygromycin in addition to the intended gene. The promoter contained in the construct may be a constitutive promoter, organ-specific promoter or developmental stage-specific promoter. The promoter can be suitably selected depending on the host, gene, desired expression level, organ for the expression, developmental stage, etc.

According to the present invention, a plant showing an excess expression of antisense mRNA of a gene encoding an enzyme for assimilating or utilizing nitrogen can be obtained by transforming plant cells with a genetic construct containing a plant promoter connected to the antisense sequence of a nucleotide sequence encoding a desired enzyme. In a preferred embodiment of the present invention, related promoters are powerful, organ-nonspecific or developmental stage-nonspecific promoters (such as promoters which strongly express in many or all tissues). An example of such powerful, constitutive promoters is CaMV35S promoter.

In another embodiment of the present invention, it is advantageous in some cases that a plant is manipulated with a genetic construct in which an organ-specific or developmental stage-specific promoter is connected to a nucleotide sequence encoding a desired enzyme. For example, when the expression in a photosynthetic tissues and organs is intended, a promoter of ribulose bisphosphate carboxylase (RuBisCO) gene or chloroplast aib binding protein (CAB) gene can be used. When the expression in seeds is intended, promoters of various seed storage protein genes can be used. When the expression in fruits is intended, a fruit-specific promoter (such as tomato 2A11) can be used. When the expression in tubers is intended, a promoter of protein genes stored in tubers (such as potato patatine) can be used.

In still another embodiment of the present invention, it can be advantageous to transform a plant with a gene construct obtained by linking a inducible promoter to a nucleotide sequence encoding a desired enzyme. Various examples of such promoters are known. They include, but are not limited to, promoters of heat shock genes, protection responding genes (such as phenylalanine ammonia lyase genes), wound responding genes (such as cell wall protein genes enriched with hydroxyproline), chemically inducible genes (such as nitrate reductase genes and chitinase genes) and dark inducible genes (such as asparagine synthetase genes (Coruzzi and Tsai, U.S. Pat. No. 5,256,558).

The recombinant nucleic acid construct of the present invention may contain a marker which can be selected for tracing the transmission of the construct. For example, an construct transmitted in bacteria contain an antibiotic-resistant gene such as a gene which allow the bacteria to be resistant to kanamycin, tetracycline, streptomycin or chloramphenicol. The vectors which is suitable to transfer the construct include plasmids, cosmids, bacteriophages and viruses. In addition, the recombinant construct may contain a marker gene which can be used for selection or a marker gene which can be screened, which genes can be expressed in a plant for isolating, identifying or tracing the plant cells transformed with the construct. The selectable markers include, but are not limited to, genes which impart resistance to an antibiotic (such as kanamycin or hygromycin) or resistance to a herbicide (such as sulfonylurea, phosphino-thricin or glyphosate). The markers which can be screened include, but are not limited to, genes encoding β-glucuronidase [Jefferson, Plant Mol. Biol. Rep 5: 387–405 (1987)], genes encoding luciferase [Ow et al., Science 234: 856–859 (1986)] and B and C1 gene products controlling the production of anthocyanin pigment.

The gene-transferring method which can be employed in the present invention is not particularly limited. Any method known in the art for transferring a gene into plant cells or plant bodies can be employed. For example, in an embodiment of the present invention, Agrobacterium can be used for introducing a genetic construct into a plant. In such a transformation, it is desirable to use Agrobacterium binary T-DNA vector [Bevan, Nuc. acid Res. 12: 8711–8721 (1984)] and co-culture [Horsch et al, Science, 227: 1229–1231 (1985)]. Agrobacterium transformation system is usually used for genetically manipulating dicotyledons [Bevans et al., Ann. Rev. Genet., 16: 357–384 (1982); and Rogers et al., Methods Enzymol., 118: 627–641 (1986)]. Agrobacterium transformation system is also usable for transforming monocotyledons or cells thereof [Hernalsteen et al., EMBO J., 3: 3039–3041 (1984); Hoykass-Van Slogteren et al., Nature, 311: 763–764 (1984); Grimsley et al., Nature, 325: 167–1679 (1987); Boulton et al., Plant mol. Biol., 12: 31–40 (1989); and Gould et al., Plant Physiol., 95: 426–434 (1991)]. When Agrobacterium system is used for the transformation of plants, the recombinant DNA construct further contains at least right border sequence of T-DNA domain at a position adjacent to DNA sequence to be introduced into plant cells. In a preferred embodiment, the sequence to be introduced is inserted between the left and right T-DNA border sequences. Suitable design and constitution of transgenic vectors based on T-DNA are well-known in the art.

In another embodiment, various methods other than those described above can be employed for introducing the recombinant nucleic acid construct into plants and plant cells. An example of other gene introduction method and transformation method is a protoplast transformation of naked DNA by calcium, polyethylene glycol (PEG) or electroporation [Paszkowski et al., EMBO J., 3: 2727–2722 (1984); Potrykus et al., Mol. Gen. Genet., 199: 169–177 (1985); Fromm et al., Proc. Nat. Acad. Sci. USA, 82: 5824–5828 (1985); and Shimamoto et al., Nature, 338: 274–276 (1989)]. According to the present invention, various plants and plant cells can be manipulated to obtain desired physiological properties described herein by using the nucleic acid construct and the transformation method of the present invention, as described above. The methods of the present invention are particularly advantageous when the target product is a monocotyledon or plant cells thereof. In a preferred embodiment, the target plants and plant cells to be manipulated are, for example, tomatoes, potatoes, beets, soybeans, Arabidopsis, corns, wheats, rice plants and sugar canes. Tomatoes are particularly preferred.

According to the present invention, an intended plant can be obtained by introducing and manipulating a gene construct as disclosed herein into various plant cells or parts of pants, for example, protoplasts, tissue-cultured cells, tissues and organ explants, pollens, embryos and whole plant bodies. From the plants manipulated according to the embodiment of the present invention, the intended transgenic plant is selected or screened by an approach and method described below. An individual plant can be regenerated from the isolated transformant. Methods of regenerating individual plants from plant cells, tissues or organs are known by those skilled in the art for various plant species.

The transformed plant cells, calli, tissues or plants can be identified and isolated by selecting or screening the characters encoded by marker genes contained in the genetic structure used for the transformation. For example, the selection can be conducted by growing a manipulated plant in a medium containing an repressive amount of antibiotic or herbicide to which the transforming genetic construct can impart the resistance to the manipulated plant. Further, the transformed plant cells and plants can be identified by screening for the activity of visible marker genes (such as β-glucuronidase genes, luciferase genes, B genes or C1 genes) which may be present in the recombinant nucleic acid construct of the present invention. The methods of the selection and screening are well known by those skilled in the art.

Physical methods and biochemical methods can be employed for identifying plants containing the genetic construct of the present invention or plant cells transformed with the genetic construct. Examples of the methods are as follows:
1) Southern analysis or PCR amplification for detecting and determining the structure of recombinant DNA insert;
2) Northern blotting, S1 RNase protection, primer elongation PCR amplification or reverse transcriptase PCR (RT-PCR) amplification for detecting and determining the RNA transcription product of genetic construct; and
3) When the product of a gene construct is a protein, protein gel electrophoresis, Western blotting, immunoprecipitation, enzyme immunoassay, and the like, can be employed. These assay methods are well known by those skilled in the art.

In the present invention, transformed plants can be screened to obtain an intended physiological change for the purpose of obtaining the plant having improved component characters. For example, when the manipulation is conducted for repressing the expression of GAD enzyme, the transformed plant can be tested for the desired reduced expression level of GAD enzyme in a desired tissue and in a desired developmental stage. Then the plant having a desired physiological change, such as reduced GAD expression, can be successively screened for a desired change in the components.

According to the present invention, plants manipulated by a modification in the process for assimilating or utilizing nitrogen have improved component characteristics. Namely, they contain a large amount of free amino acids, particularly glutamic acid, asparagine, aspartic acid, serine, threonine, alanine and histidine. Among these amino acids, glutamic acid usable as a tasty component is contained particularly in a large amount. The manipulated plants and plant lines having such improved characteristics can be identified by determining free amino acid contents of the plants. The operation and method of the analysis are well known by those skilled in the art.

The plants obtained by the present invention have free amino acid contents higher than those of control plants (parent plants). In a preferred embodiment, free amino acid content, particularly glutamic acid (tasting component) content in edible parts such as fruits, roots and seeds of a desired plant is increased to at least twice as high as that of the parent. The total free amino acid content is also increased to at most about 3 times as high as that of the parent. As for amino acids other than glutamic acid, the increase in amount of aspartic acid, asparagine, alanine, serine, threonine and histidine is particularly remarkable. Although the kinds of plants having an amino acid composition which can be improved by the present invention are not particularly limited, tomatoes containing glutamic acid as the main tasting component are particularly preferred.

The following Examples will concretely illustrate the present invention. In the following Examples, tomato plants were manipulated by genetic engineering techniques with recombinant constructs comprising the nucleotide sequence encoding tomato GAD gene connected in antisense direction to cauliflower mosaic virus (CaMV) 35S promoter which is a powerful constituent plant promoter.

EXAMPLE 1

Isolation of GAD Gene Derived from Tomato

The inorganic salts of MS medium [Murashige and Skoog, Physiol. Plant., 15: 473–479 (1962)](Wako Pure Chemical Industries, Ltd.) and MS vitamin were used for tomato seeds. At first, tomato seeds surface-sterilized with 70% ethanol (30 seconds) and 2% sodium hypochlorite (15 minutes) were placed in plant hormone-free MS agar medium, and cultured at 25° C. for one week while the daylight hours were kept to be 16 hours to obtain sterile plants. Total RNA was prepared from the roots of the obtained juvenile plants.

mRNA was purified from total RNA with Poly (A) Quick mRNA Isolation Kit (Stratagene Co.) and then first-strand cDNA was produced with First-Strand cDNA Synthesis Kit (Amersham Pharmacia Biotech Co.). First-strand cDNA thus obtained was then used for PCR reaction as a template. The PCR reaction was conducted with PCR system 2400 (Perkin Elmer) as follows: 35 cycles of 94° C.-3 minutes, 94° C.-45 seconds, 59° C.-30 seconds, 72° C.-90 seconds; and then 72° C.-10 minutes. The primers used are shown in Table 1. Obtained PCR products were cloned using TA-Cloning Kit (Invitrogen Co.). The nucleotide sequences were determined using six plasmids containing inserts of intended size by 377A Sequencer(ABI Co), and the homology between them and the known GAD gene [Gallego et al., Plant Mol. Biol., 27; 1143–1151 (1995)] was examined. Among the obtained clones, the nucleotide sequence of T-gad-19 gene is shown in SEQ ID:1.

TABLE 1

Primer DNA used for PCR reaction

| | | |
|---|---|---|
| a | 5'-region -CCA AAG GAA GCA GCA TAT CAG ATC AT-3'-region | (26 mer)(SEQ ID:2) |
| | 5'-region -TCG GCG AGT GTA CGG GAG AAA TCT TC-3'-region | (26 mer)(SEQ ID:3) |
| b. | 5'-region -CCC CTC GGT ATC CAA TTA GAG-3'-region | (21 mer)(SEQ ID:4) |
| | 5'-region -CGG GGG GTG GGC GAA GAA CTC CAG-3'-region | (24 mer)(SEQ ID:5) | a. GAD gene specific primer [Gallego et al. Plant Mol. Biol., 27; 1143–1151 (1995), PCR product, about 1.1 kbp]
b. Primer which is ampblied between Nos-promoter and NPTII (PCR product, 1.0 kbp)

The results were as follows: There were no inserts having completely identical nucleotide sequence to the sequence of known tomato GAD gene [Gallego et al., Plant Mol. Biol., 27; 1143–1151 (1995)]. In the tested clones, T-gad-19 gene (SEQ ID:1) had the highest homology (85%). It was decided to use T-gad-19 gene because this gene was judged to be functional in the antisense method.

EXAMPLE 2

Subcloning of Tomato GAD Gene (T-gad-19) into Ti-plasmid (pMAT037)

Figure 1:
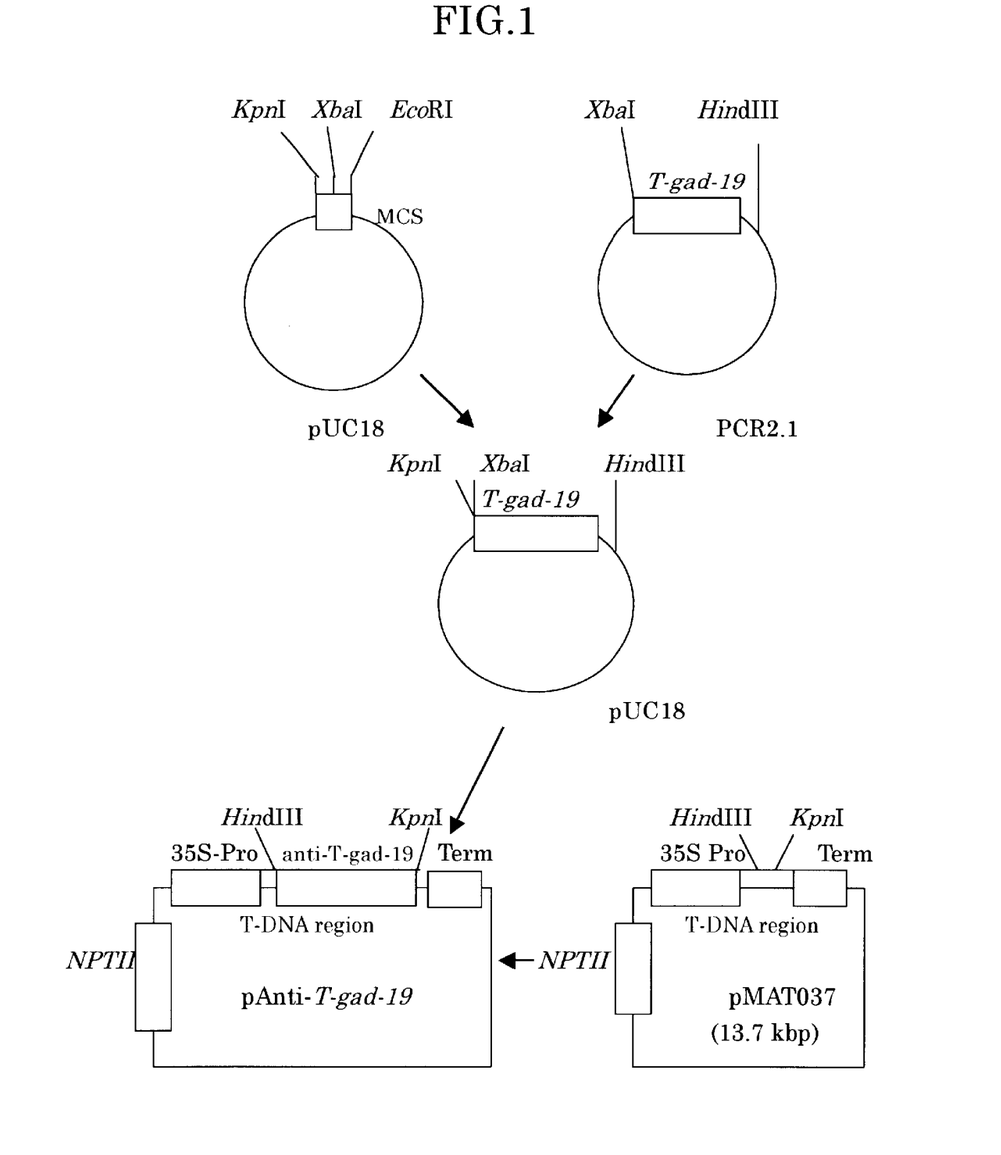
FIG. 1 shows a circular map of the plasmid vector pAnti-T-gad-19. 35S Pro:CaMV 35S promoter, Term, teminator.

T-gad-19 gene derived from a tomato cloned into PCR2.1 vector was subdloned into Ti plasmid (pMAT037) [Matsuoka and Nakamura, Proc. Natl. Acad. Sci. USA, 88: 834–838 (1991)] which is the vector for plant transformation. At first, the T-gad-19 gene fragment was obtained using restriction sites Xba I and Hind III in PCR 2.1 vector and Xba I and Hind III sites on multicloning site of pUC 18 were replaced by the fragment. The plasmid was further digested with restriction enzymes Kpn I and Hind III. After the introduction of the KpnI-HindIII fragment into Kpn I-Hind III region in the multicloning site located after CaMV 35S promoter of pMAT037, *E. coli* DH 5α was transformed with the construct. Ti plasmid into which anti-T-gad-19 gene had been introduced was transferred into Agrobacterium EHA 101 strain (FIG. 1) and used for the infection of tomatoes.

EXAMPLE 3

Production of Transgenic Plant By the Infection of Tomato Cotyledons With Agrobacterium Tomato (cultivar, minitomato) seeds were surface-sterilized with 70% ethanol (30 seconds) and 2% sodium hypochlorite (15 minutes), and then placed on a plant hormone-free MS agar medium. The seeds were cultured at 25° C. for one week while the daylight hours were kept to be 16 hours. The cotyledons were taken from the obtained sterile juvenile plants, then placed on an MS agar medium containing 2 mg/l of Zeatin and 0.1 mg/l of IAA (regeneration medium in 9 cm Petri dish), and cultured under the same conditions as those described above for 2 days. Agrohacterium (EHA 101) containing pAnti-T-gad-19 was cultured in YEP medium (Table 2) overnight and used for the infection. The cotyledons cultured for two days were collected in a sterilized Petri dish, and the Agrohacterium suspension was added to them to cause the infection. Supeirfluous Agrohacterium suspension was removed from the cotyledons by using a sterilized filter paper. After further removing superfluous Agrohacterium suspension, a sterilized filter paper was placed on the medium in the above-described Petri dish in order to prevent rapid propagation of Agrobacterium. The infected cotyledons were placed thereon. After co-culture for 24 hours, the cotyledons were transferred into MS regeneration medium (selecting medium) containing 50 mg/l of kanamycin and 500 mg/l of claforan to select the transformant. The regenerated shoots were transferred into a new selecting medium to conduct further selection. Well-grown green shoots were cut at the stems and transferred into a plant hormone-free MS medium (rooting medium in a test tube). The rooted, regenerated plant sequentially acclimated to the soil.

TABLE 2

| Composition of YEP medium | (1 liter) |
|---|---|
| Bactotrypton | 10 g |
| Yeast extract | 10 g |
| glucose | 1 g |

EXAMPLE 4

Confirmation of Introduced Gene

Total DNA was extracted by the method of Honda et al. [Honda and Hirai, Jpn. J. Breed 40, 339–348 (1990)] from 4 selected individual plants obtained by the infection with Agrobacterium containing pAnti-T-gad-19, 3 plant individuals obtained by the infection with Agrobacterium (containing only Ti plasmid) free of the intended gene, and 2 plant individuals obtained directly from the regeneration from cotyledons without Agrobacterium treatment. DNA thus extracted was purified by RNase treatment, phenol/chloroform treatment and PEG precipitation. The purified product was diluted to 0.01 µg/µl and used as a template for PCR. PCR reaction was conducted with a primer (b in Table 1) capable of obtaining about 1.0 kbp of amplification products on the basis of the sequence from NPT II gene to the sequence in Nos-Promoter on T-DNA of Ti plasmid. The reaction conditions were as follows: 35 cycles under conditions of 94° C.-1 minute, 55° C.-1 minute and 72° C.-2 minutes. The PCR product was subjected to the electrophoresis with 1% agarose gel and then stained with ethidium bromide.

Figure 2:
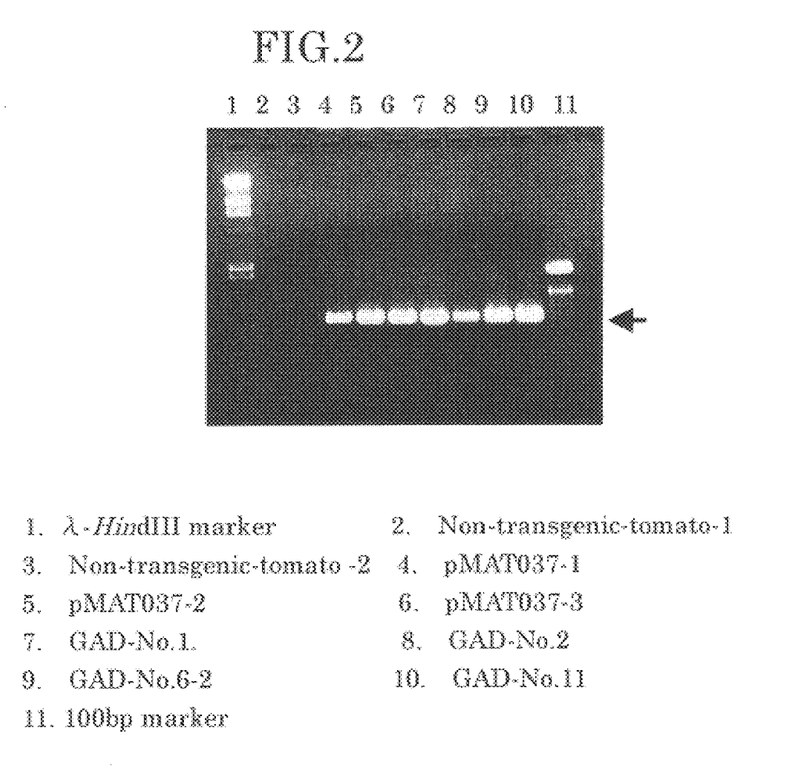
FIG. 2 shows the results of PCR analysis of tomato transformed with anti-T-gad 19 gene of tomato. 94° C.-1 minute, 55° C.-1 minute, 72° C.-2 minutes, 35 cycles). Symbols of the respective samples are the same as those shown in Table 3. non-transgenic tomatoes (Cont-1, Cont-2); transgenic tomatoes having plasmid pMAT037 introduced therein; transgenic tomatoes having anti-T-gad-19 gene introduced therein (GAD-1, GAD-2, GAD-6-2, GAD-11).

A band of about 1.0 kbp, which has an expected band size, was confirmed in individual plants infected with Agrobacterium containing pAnti-T-gad-19 and also in individuals infected with Agrobacterium containing plasmid gene(FIG. 2). These results suggested that the gene had been introduced into the obtained transformed plants.

EXAMPLE 5

Extraction and Determination of Free Amino Acids

Fruits of the transgenic plants obtained in Example 4 were harvested 6 weeks after the blossom, and stored at −80° C. Each fruit was cut into about 6 pieces, weighed, fed into a mortar, frozen with liquid nitrogen and ground. 3 ml of 80% ethanol was added thereto, and the obtained mixture was further thoroughly ground, transferred into a centrifugal tube and incubated at 80° C. for 20 minutes. After the centrifugation at 10,000 rpm for 20 minutes, the supernatant was transferred into another tube. 2 ml of 80% ethanol was added to the remaining pellets, and the pellets were ground again in the mortar and then incubated at 80° C. for 20 minutes. After the centrifugation, the supernatant was transferred into the tube combining with the previously obtained supernatant to obtain a mixture. The total amount of the mixture was adjusted to 5 ml with 80% ethanol. After thorough mixing, 20 µl of the mixture was taken, dried and dissolved in 0.02 N hydrochloric acid. After the filtration through a 0.45 µm filter, a sample for the analysis was obtained. The amino acid analysis was conducted with Hitachi high-speed amino acid analyzer (L-8800). The results of the amino acid analysis of transgenic tomatoes having GAD antisense gene are shown in Table 3 together with the results of the amino acid analysis of tomatoes into which only Ti plasmid had been introduced.

cultured in an outdoor closed system greenhouse in order to increase the number of fruits per plant. To make the nutrition conditions uniform, no additional fertilizer was given after

TABLE 3

Amino acid content of fruits of transgenic tomatoes into which Anti-T-gad-19 gene was introduced

|  | Asp | Thr | Ser | Asn | Glu | Gln | Gly | Ala | Val | Met |
|---|---|---|---|---|---|---|---|---|---|---|
| Non-transgenic tomato |  |  |  |  |  |  |  |  |  |  |
| Control-1 | 1309 | 98 | 143 | 261 | 8876 | 680 | 22 | 295 | — | 15 |
| Control-2 | 1043 | 70 | 137 | 211 | 8482 | 394 | 20 | 221 | — | 19 |
| Plasmid(pMAT037) |  |  |  |  |  |  |  |  |  |  |
| pMAT-1 | 1326 | 139 | 316 | 232 | 6003 | 697 | 43 | 660 | 98 | 24 |
| pMAT-2 | 1998 | 195 | 371 | 227 | 11182 | 497 | 65 | 828 | — | 76 |
| pMAT-3 | 1280 | 217 | 439 | 368 | 3273 | 854 | 146 | 129 | 177 | 30 |
| Transgenic tomato |  |  |  |  |  |  |  |  |  |  |
| (anti-T-gad-19) |  |  |  |  |  |  |  |  |  |  |
| GAD-1 | 5067 | 467 | 692 | 978 | 17558 | 3733 | 134 | 1442 | — | 48 |
| GAD-2 | 1921 | 288 | 573 | 547 | 17920 | 1664 | 166 | 1309 | 194 | 72 |
| GAD-6-2 | 2593 | 184 | 444 | 309 | 15493 | 633 | 81 | 1041 | — | 30 |
| GAD-11 | 2465 | 202 | 361 | 406 | 14579 | 623 | 49 | 415 | — | 47 |

(nmol/g.F.W.)

Figure 3:
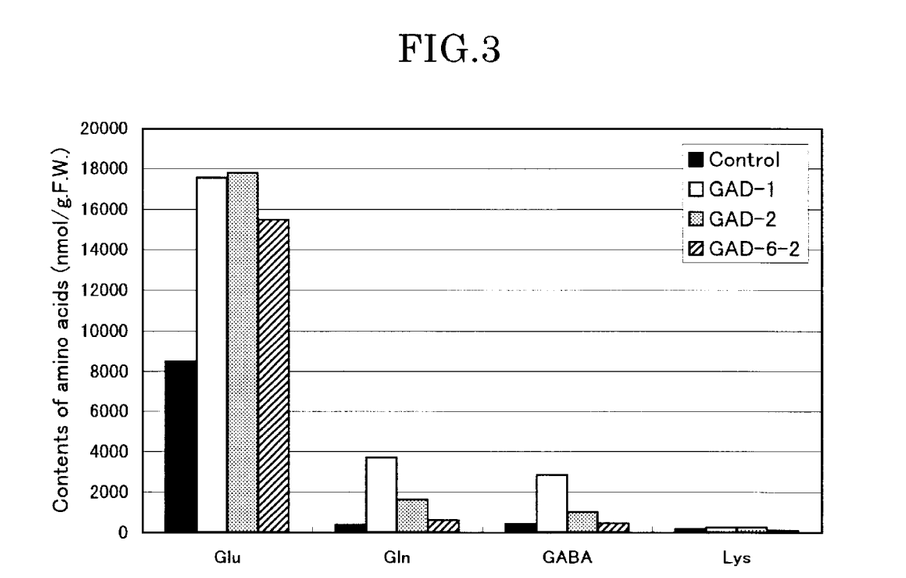
FIG. 3 shows amino acids contents in fruits of tomato transformed with anti-T-gad gene of tomato (GAD-1, GAD-2, GAD-6-2) (glutamic acid—Glu, glutamine—Gln, γ-aminobutyric acid—GABA, lysine—Lys).

In the tested 4 transgenic lines, lines having an increased amino acid content, particularly glutamic acid content increased to at least twice as high as the control were GAD-1 and GAD-2. In these lines, other amino acid content, particularly asparagine, aspartic acid, serine, threonine, alanine and histidine content, was also increased (Table 3). Glutamic acid contents of GAD-1 and GAD-2 were 2.02 times and 2.06 times as high, respectively, as that of the control. Glutamine contents of them were 6.95 times and 3.10 times as high, and GABA contents of them were as high as 6.42 times and 2.29 times as high as that of the control(FIG. 3).

EXAMPLE 6

Analysis of Subsequent Generations of Anti-T-gad 19 Gene Introduced Tomatoes

1) Northern Analysis

Total RNA was extracted from leaf tissue of a lateral bud of transformant ($T_0$ generation) by phenol/SDS method. 20 μg of total RNA was subjected to the electrophoresis with formaldehyde-agarose gel (1.0%), and then transferred on a nylon membrane. The obtained product was then subjected to Northern hybridization with a DIG-labeling and Detection Kit (Rosche Molecular Biochemicals). T-gad-19 gene was used as the probe.

Figure 4:
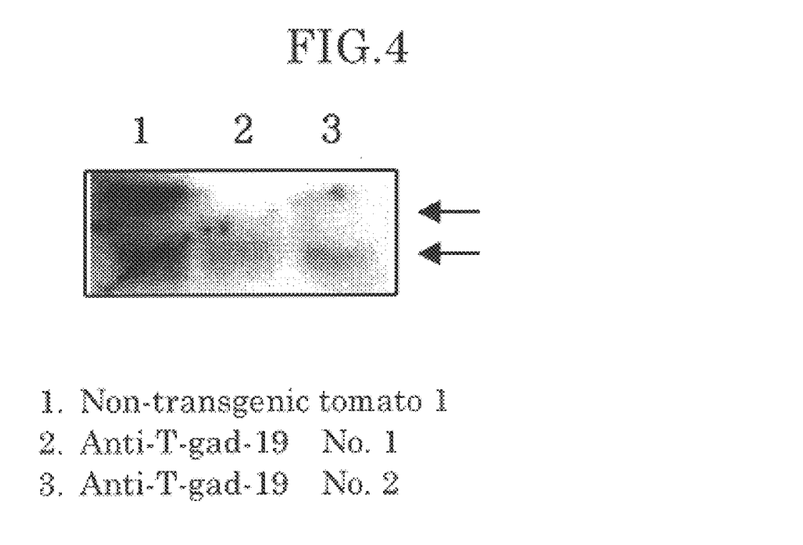
FIG. 4 shows the results of Northern hybridization conducted with T-gad-19 gene as the probe confirmed that Anti-T-gad-19 gene introduced plant line Nos. 1 and and 2 demonstrated the decreased level of GAD gene expression.

Northern hybridization conducted with T-gad-19 gene as the probe confirmed that Anti-T-gad-19 gene introduced plant line Nos. 1 and 2 demonstrated the decreased level of GAD gene expression (FIG. 4). However, because plant line No. 1 seeds did not germinate, the analysis of the progeny was impossible.

2) Selection of $T_1$ Generation

Seeds of transformed tomato ($T_0$ generation) obtained by introducing a gene by Agrobacterium method were surface-sterilized with 80% ethanol for 30 seconds and 2% sodium hypochlorite for 15 minutes, and then sterilely placed on MS agar medium containing 350 mg/l of kanamycin under sterile conditions. One month later, well-grown plants were selected and acclimatized to the soil. The plants were cultured in an outdoor closed system greenhouse in order to increase the number of fruits per plant. To make the nutrition conditions uniform, no additional fertilizer was given after the transplantation into 1 kg of culture soil (Power soil; Sakata no Tane) during acclimation to the soil.

Seeds of the transformant of the subsequent generation ($T_1$) were selected on an agar medium containing 350 mg/l of kanamycin, an antibiotic, under sterile conditions. As a result, kanamycin-resistant plant lines GAD 2-2-1, GAD 2-2-2, GAD 2-2-3 and GAD 2-3-1 could be selected from Anti-T-gad-19 gene-introduced plant line No. 2.

3) Determination of Amino Acid Content of Fruits

Three fruits taken in the 6th week after blossoming of the first fruit cluster were used for the analysis. 3 parts by weight of 80% ethanol heated to 80° C. was added to 1 part by weight of the fruits. The obtained mixture was ground in a mortar and then heated again to 80° C. for 20 minutes. After the centrifugation at 7,000 rpm, the obtained supernatant liquid was recovered. After the addition of 80% ethanol, the obtained mixture was heated to 80° C. The extraction with ethanol was conducted three times, and the obtained extracts were combined together and then 80% ethanol was added thereto to make the total amount 100 ml. After through mixing, 200 μl of the extract was taken in an Eppendorf tube, dried and then dissolved in 200 μl of sterilized water. 200 μl of ethyl ether was added to the obtained solution, and they were mixed together and then centrifuged at 12,000 rpm. The ether layer was removed. The aqueous layer was dried again and dissolved in 200 μl of 0.02 N HCl. The resultant solution was filtered through a 45 μm filter, and the filtrate was taken as a sample and analyzed with Hitachi high-speed amino acid analyzer (L-8800).

Figure 5:
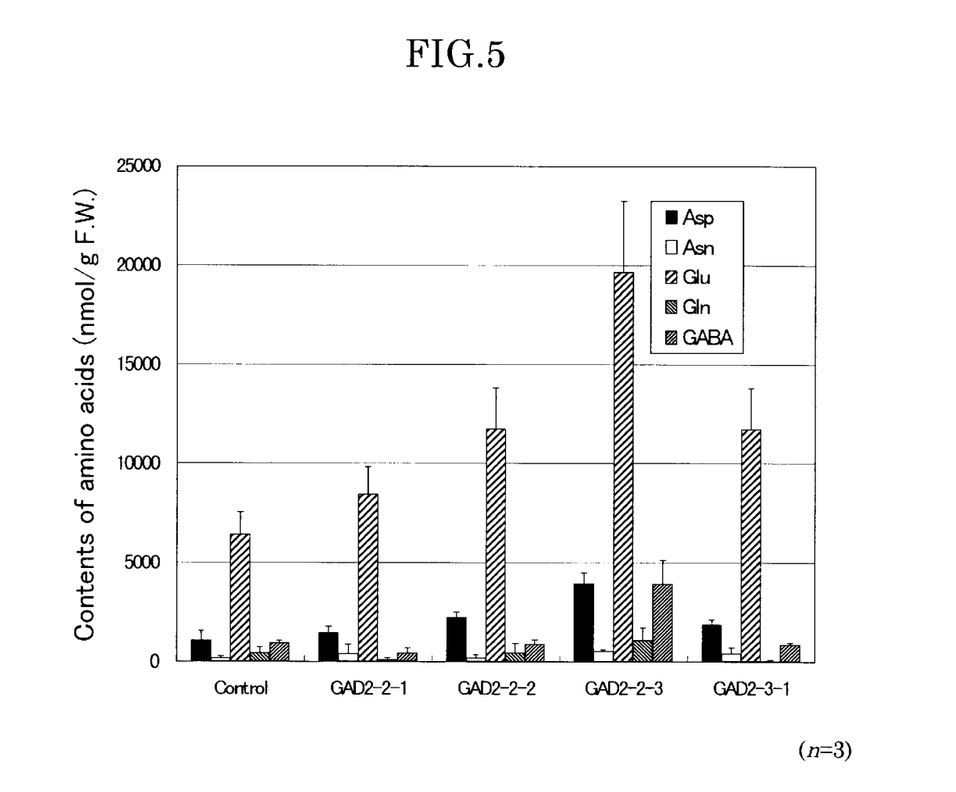
FIG. 5 shows the results of the amino acids extracted from three fruits of the transformed first fruit cluster to determine amino acid content of the fruits as described in Example 6. The results were shown by the average of the three fruits. Glu contents of GAD 2-2-1, GAD 2-2-2, GAD 2-2-3 and GAD 2-3-1, which were the subsequent generations of Anti-T-gad-19 gene-introduced plant line No. 2, were increased to 1.3 times, 1.8 times, 3.0 times and 1.8 times as high as that of the untransformed fruit.

Amino acids were extracted from three fruits of the transformed first fruit cluster to determine amino acid content of the fruits. The results were shown by the average of the three fruits. Glu contents of GAD 2-2-1, GAD 2-2-2, GAD 2-2-3 and GAD 2-3-1, which were the subsequent generations of Anti-T-gad-19 gene-introduced plant line No. 2, were increased to 1.3 times, 1.8 times, 3.0 times and 1.8 times as high as that of the untransformed fruit (Table 4, FIG. 5). As for amino acids other than Glu, Ala was remarkably increased, and in some plant lines, Asp content and/or Asn content were increased. The total free amino acid content was also increased to the maximum of 3.2 times compared with that of the untransformed plants.

TABLE 4 amino acids contents in fruits of tomato transformed with anti-gad-19 gene of tomato

| | Asp | Thr | Ser | Asn | Glu | Gln | Gly | Ala |
|---|---|---|---|---|---|---|---|---|
| Control | 1093 | 100 | 220 | 184 | 6416 | 443 | 14 | 287 |
| | (484)[a] | (33) | (51) | (91) | (1156) | (331) | (8) | (111) |
| GAD2-2-1 | 1471 | 131 | 324 | 396 | 8442 | 104 | 22 | 555 |
| | (311) | (9) | (46) | (502) | (1389) | (98) | (5) | (226) |
| GAD2-2-2 | 2224 | 177 | 394 | 181 | 11745 | 451 | 35 | 800 |
| | (282) | (11) | (59) | (171) | (2087) | (482) | (11) | (248) |
| GAD2-2-3 | 3960 | 311 | 743 | 542 | 19674 | 1108 | 71 | 1146 |
| | (561) | (30) | (86) | (76) | (3566) | (624) | (16) | (458) |
| GAD2-3-1 | 1877 | 153 | 412 | 385 | 11747 | 36 | 28 | 684 |
| | (259) | (11) | (54) | (342) | (2089) | (62) | (5) | (11) |

| | Val | Met | Ile | Leu | Tyr | Phe |
|---|---|---|---|---|---|---|
| Control | 85 | 19 | 38 | 42 | 47 | 87 |
| | (54) | (9) | (18) | (9) | (5) | (36) |
| GAD2-2-1 | 135 | 24 | 53 | 44 | 36 | 104 |
| | (35) | (6) | (5) | (5) | (15) | (12) |
| GAD2-2-2 | 130 | 26 | 96 | 81 | 56 | 155 |
| | (10) | (2) | (16) | (17) | (7) | (37) |
| GAD2-2-3 | 134 | 44 | 178 | 152 | 87 | 427 |
| | (28) | (6) | (47) | (19) | (7) | (74) |
| GAD2-3-1 | 117 | 25 | 70 | 63 | 44 | 91 |
| | (16) | (5) | (1) | (3) | (7) | (11) |

| | GABA | Lys | His | Arg | Pro | Total |
|---|---|---|---|---|---|---|
| Control | 961 | 43 | 127 | 118 | 37 | 10363 |
| | (108) | (16) | (41) | (167) | (42) | (4235) |
| GAD2-2-1 | 432 | 56 | 173 | 19 | 48 | 12569 |
| | (254) | (12) | (56) | (33) | (43) | (2174) |
| GAD2-2-2 | 891 | 85 | 251 | 26 | 47 | 17851 |
| | (237) | (7) | (30) | (44) | (58) | (1916) |
| GAD 2-2-3 | 3956 | 204 | 363 | 49 | 227 | 33374 |
| | (1182) | (23) | (48) | (85) | (44) | (4381) |
| GAD 2-3-1 | 880 | 64 | 253 | 0 | 33 | 16964 |
| | (65) | (25) | (56) | (0) | (58) | (2469) |

[a]Values in parentheses are standard error. (n = 3) (nmol/g.F.W.)

According to the present invention, plants containing free amino acids in a high concentration can be obtained. Thus, crops usable as starting materials and food materials having a high added value, particularly tomatoes having a particularly high added value, are provided. According to the present invention, the whole free amino acid content is increased to the maximum of about 3-times. Particularly crops containing a very high concentration of at least one of glutamic acid, asparagine, aspartic acid, serine, threonine, alanine and histidine are provided. Thus, crops to be used as starting materials having a high added value and necessitating no further addition of these amino acids are provided. Further, according to the present invention, food materials containing a high concentration of glutamic acid accumulated therein, namely food materials having a good taste, can be provided.

In addition, the period for breeding plants containing such free amino acids in a high concentration is remarkably shortened according to the present invention.

What is claimed is:

1. A method of producing a transgenic tomato containing, in a fruit of the transgenic tomato, one or more free amino acids in an amount larger than that contained in the same natural plants cultured under the same conditions, which comprises the steps of
   a) transforming a tomato with a genetic construct containing the antisense sequence of a gene encoding glutamate decarboxylase (GAD), a regulatory sequence capable of expressing the antisense sequence and a marker gene, wherein said gene encoding GAD has the sequence having at least 85% homology to a sequence of SEQ ID NO: 1;
   b) selecting or identifying the transgenic tomato based on a character imparted by the marker gene in the genetic construct;
   c) screening the transgenic tomato in which one or more free amino acids are accumulated in a larger amount; and
   d) selecting the transgenic tomato in which one or more free amino acids are accumulated in a larger amount.

2. The method according to claim 1, wherein the genetic construct contains the antisense GAD nucleotide sequence functionally connected to a constitutive promoter for the tomato plant.

3. The method according to claim 2, wherein the genetic construct is an antisense GAD fusion gene comprising anti-T-gad-19 gene derived from a tomato GAD gene and CaMV 35S.

4. The method according to claim 1, wherein the free amino acid is selected from the group consisting of asparagine, aspartic acid, serine, threonine, alanine, histidine and glutamic acid.

5. The method according to claim 1, wherein one of the free amino acids is free glutamic acid.

6. The method according to claim 1, wherein the genetic construct contains the antisense sequence of the gene encoding GAD functionally connected to a constitutive promoter for the tomato, and the accumulated amino acid is glutamic acid.

7. A transgenic tomato produced by the method according to claim 1 or a progeny of the transgenic tomato wherein the progeny contains the genetic construct containing the antisense sequence of the gene encoding GAD.

8. A transgenic tomato produced by the method according to claim 1, wherein the total amino acid content of the fruit is at least twice as high as that of corresponding natural plants, or a progeny of the transgenic plant wherein the progeny contains the genetic construct containing the antisense sequence of the gene encoding GAD and the total amino acid content of the fruit of the progeny is at least twice as high as that of corresponding natural plants.

9. A transgenic tomato produced by the method according to claim 1, wherein free glutamic acid content of the fruit is at least twice as high as that of corresponding natural plants, or a progeny of the transgenic plant wherein the progeny contains the genetic construct containing the antisense sequence of the gene encoding GAD and the total amino acid content of the fruit of the progeny is at least twice as high as that of corresponding natural plants.

10. Seeds of the transgenic tomato or seeds of the progeny according to claim 7, which contains the antisense sequence of a gene encoding GAD, wherein said gene encoding GAD has the sequence having at least 85% homology to the sequence of SEQ ID NO:1.

11. The according to claim 1, wherein said gene encoding GAD has the sequence of SEQ ID NO:1.

12. The method according to claim 1, wherein said marker gene is a drug-resistance or herbicide resistance gene.

13. The method according to claim 12, wherein said drug-resistance or herbicide resistance gene is a gene for resistance to a drug or herbicide selected from the group consisting of kanamycin, tetracycline, streptomycin, chloramphenicol, sulfonylurea, phosphinothricin, glyphosate, G 418, and hygromycin.

14. The method according to claim 1, wherein said transforming is by a method selected from the group consisting of a Agrobacterium transformation method, a protoplast transformation method using calcium, a protoplast transformation method using polyethylene glycol, and a protoplast transformation method using electroporation.

* * * * *

SEQUENCE LISTING

<160> NUMBER OF SEQ ID NOS: 5

<210> SEQ ID NO 1
<211> LENGTH: 1180
<212> TYPE: DNA
<213> ORGANISM: Lycopersicon esculentum

<400> SEQUENCE: 1

```
ccaaaggaag cagcatatca gattctaaat gatgaactta tgttagatgg aaatccaagg      60
ttgaatttgg catcttttgt gacaacatgg atggaaccag aatgtgacaa attgatgatg     120
gattccatta acaaaaatta tgttgacatg gatgaatatc ctgtcaccac tgagcttcag     180
aatcggtgtg taaacatgat agcgcattta tttaatgcac cacttgaaga tggagaaact     240
gcagttggag ttggaacagt tggttcttca gaagccatta tgcttgctgg attggccttt     300
aagagaaaat ggcaaaacaa aatgaaagcc caaggaaagc cctatgataa gcccaacatt     360
gttactggtg ctaatgtcca ggtgtgttgg gaaaaatttg caaggtattt tgaagttgag     420
ctaaaagaag tgaagttgac tgatggatac tatgtgatga gccctgagaa agctgtggaa     480
atggttgatg agaacacaat ttgtgtagct gctattttgg gttcaactct gaatggggag     540
tttgaggaag tgaagaaatt gaatgacctc ctattgaaaa gaacaaggaa acagggtggg     600
acactccaat tcatgtggat gcagctagtg gtggatttat tgcaccattt atatatccag     660
aacttgaatg ggactttaga ttgccattag ttaaaagtat aaatgtcagc ggtcacaagt     720
atggccttgt atatgctggt gtcggttggg tcatatggcg gagcaaggaa gacttgcccg     780
```

```
atgaacttat ttttcatatt aattaccttg ggtctgatca acctactttc accctcaatt      840
tctctaaagg atcaagtcaa gtaattgctc aatattatca actaattcgt tttggttatg      900
agggttataa gaacgtcatg aagaattgct tatcaaacgc aagggtacta acagagggaa      960
tcacaaaaat gggaagattc gagattgtct ccaaggatgt tggtgttccc ttggttgcat     1020
tttctcttaa agacaatagc aaacatgatg agtttgaagt atctgaaact ttaaggagat     1080
ttggatggat tgttccagca tacactatgc caccagatgc tcaacacatc acagttctta     1140
gagttgttat tagagaagat ttctcccgta cactcgccga                           1180

<210> SEQ ID NO 2
<211> LENGTH: 26
<212> TYPE: DNA
<213> ORGANISM: Artificial SequencE
<220> FEATURE:
<223> OTHER INFORMATION: SYNTHETIC DNA

<400> SEQUENCE: 2
ccaaaggaag cagcatatca gatcat                                            26

<210> SEQ ID NO 3
<211> LENGTH: 26
<212> TYPE: DNA
<213> ORGANISM: ARTIFICIAL SEQUENCE
<220> FEATURE:
<223> OTHER INFORMATION: SYNTYHETIC DNA

<400> SEQUENCE: 3
tcggcgagtg tacgggagaa atcttc                                            26

<210> SEQ ID NO 4
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
cccctcggta tccaattaga g                                                 21

<210> SEQ ID NO 5
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 5 cgggggggtgg gcgaagaact ccag                                             24
```